United States Patent [19]

Curutchet

[11] 4,140,123
[45] Feb. 20, 1979

[54] LANCETS

[76] Inventor: Pedro D. Curutchet, Sarmiento 156, 7635 Lobería, Argentina

[21] Appl. No.: 813,777

[22] Filed: Jul. 7, 1977

[51] Int. Cl.² .............................................. A61B 17/32
[52] U.S. Cl. .................................. 128/314; 128/305; 81/428 R; 81/177 C; 30/340
[58] Field of Search .............. 128/314, 318, 321, 322, 128/346, 305, 315, 317, 303 R, 320, 325; 30/232, 244, 249, 250, 252, 298, 314, 340, 341, 194; 32/46; 81/428 R, 415, 177 C

[56] References Cited

U.S. PATENT DOCUMENTS 1,438,374  12/1922  Guerrero ............................ 30/341 X

FOREIGN PATENT DOCUMENTS 1094820  5/1955  Argentina ................................ 128/305

Primary Examiner—Henry J. Recla

Attorney, Agent, or Firm—Ladas, Parry, Von Gehr, Goldsmith & Deschamps

[57] ABSTRACT

A bistoury handle comprises first and second elongate members, the first member being provided at one end with means for gripping a blade and having a straight portion extending from that end and a curved portion extending from the straight portion towards its opposite end. The second elongate member is straight and is joined at one end to the first elongate member at a point adjacent to the blade-gripping means and is joined at its other end to the opposite end of the first elongate member. The handle further comprises a plate-like member secured to the second elongate member intermediate the ends thereof. The curvature of the curved portion of the first elongate member is adapted to fit in the hollow of the hand while the middle and ring fingers extend about the second elongate member, one on each side of the plate-like member.

2 Claims, 3 Drawing Figures

U.S. Patent        Feb. 20, 1979        4,140,123
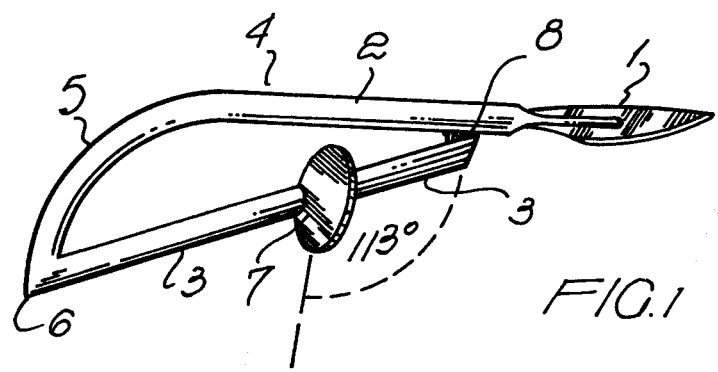
FIG. 1
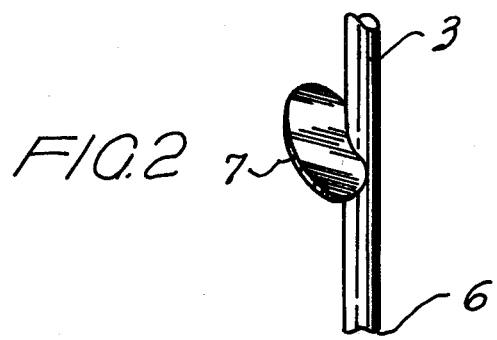
FIG. 2
FIG. 3
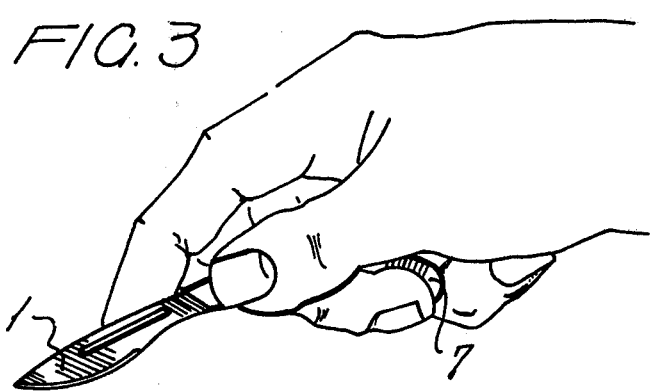

LANCETS

This invention relates to bistoury handles.

Two types of bistoury are at present known in the art, namely, the classical type having a prismatic "Collin" handle, and the "American" type having a flat handle; a bistoury may be said to be an "aximanual" instrument, since when it is taken by the hand it is oriented forwardly following the longitudinal axis of the user's hand like a knife or fork, or a fencing foil: a simple instrument that has to be oriented forwardly and depthwise necessarily must follow the same axis of the hand when used for carrying out any work as, for example, beneath the hood of an automobile.

However, even though all bistouries used in history have been and still are "aximanual", they are hardly of rational design since undivided attention is required for holding and guiding them; their apparent simplicity and ease paradoxically give rise to great complications. Thus, it is complicated to guide them because the fingers control the instrument not easily but with difficulty; it is not easy to cut when operating; the safety is incomplete and precarious since the handle of the bistouries lacks the necessary configuration and elements for being grasped.

The Collin handle is of fusiform prismatic shape that is well suited for use in performing a circular amputation but is inadequate for manipulation with the fingers. The Collin handle also tends to slip between the fingers, and its use in many countries was abandoned in favor of the American handle. The American handle is flat and therefore partly overcomes the tendency of the Collin handle to rotate. However, it is uncomfortable, since the fingers are excessively crowded, and it is too small to grip properly, as in evidenced by the grooves engraved in the handle in an attempt to overcome its tendency to slip between the fingers.

According to the present invention there is provided a bistoury handle comprising first and second elongate members each having first and second ends, the first elongate member being provided at its first end with means for gripping a blade and having a straight portion extending from its first end and a curved portion extending from said straight portion towards its second end, said second elongate member being straight and being joined at its first end to the first elongate member at a point adjacent said first end thereof and being joined at its second end to the first elongate member at said second end thereof, and the handle further comprising a plate-like member secured to the second elongate member intermediate the ends thereof, the angle, measured in the common plane of the second elongate member and the straight portion of the first elongate member, between the plane of the plate-like member and the longitudinal axis of the second elongate member lying between the plate-like member and the first end of the second elongate member being substantially in the range from 112° to 115°, and the angle, measured in the plane perpendicular to said common plane and including said longitudinal axis, between the plane of the plate-like member and said longitudinal axis lying between the plate-like member and said second end of the second elongate member being substantially in the range from 65° to 75°, the curvature of the curved portion of the first elongate member being adapted to fit in the hollow of the hand while the middle and ring fingers extend about the second elongate member, one on each side of said plate-like member.

An embodiment of the invention will now be described by way of example with reference to the accompanying drawing:

FIG. 1 is an external side view of the bistoury.

FIG. 2 is an underneath plan view of a portion of the handle.

FIG. 3 is a view in perspective to show the instrument held in the hand.

The cutting blade 1 of the bistoury and the mechanism for fitting it in the handle are known and therefore they are not described herein.

The handle is comprised of two members in the form of an upper rod 2 and a lower rod 3.

The two rod members, when connected at their ends, form an ogival window. The upper rod member 2 is straight in its front portion 4 and curved in its rear portion 5 in order to be anatomically adapted to the hollow of the hand and become stationary by spontaneously fitting into said hollow.

The lower rod member 3 is straight and forms towards the rear, where it joins the upper member, a salient angle 6.

The rod members can be hollow and light, but they can be made of any material.

Between the ends of the straight rod member 3 is fitted a small stabilizer sheet 7 the outline of which has the shape of a French bean. The sheet is welded to the lower edge of the member 3 that it diagonally crosses forming an angle of 70° that opens to the rear. The plane of the stabilizer sheet forms with the lower outline of the rod member 3 an angle of from 112° to 115° that opens to the front and downwards.

The connection of the members 2 and 3 at the front of the handle forms a short groove 8 in which the tip of the thumb fits and remains fixed.

Said groove and the width made up by the two rod members put together offer an ondulated broad surface where the tip of the thumb finds effective support. But the two most important supports are the fitting of the curved rear portion 5 in the hollow of the hand, and most of all the pressure of the middle finger upon the oblique stabilizer sheet 7. Combining these three supports plus the pressure of the little and ring fingers and the contact of the latter with the stabilizer sheet 7, there is obtained a total, firm, safe, spontaneous, almost unnoticed grasp. The dangers of rotation and slippage and, the insecurity of the other bistouries do not exist here.

The index finger resting on the blade adjusts at will its distance from the tip of the blade so that the incision starts with a small stroke, "a blow", that automatically guides the blade to the necessary depth and not more, the index finger then sliding in the direction in which the incision is to be made in a manner such that the path of the blade has a constant depth. This is analogous to the operation of the marking-gauge used by carpenters for marking a parallel line. In this case the line is parallel with the skin surface. The safety is such that the layman, once instructed, can make an incision with more safety and uniformity of precision than could be done by the most skilled surgeon. It is possible thus to calculate incisions of two millimeters.

The lancet may also be gripped putting the index finger to one side next to the middle finger, which is useful and quick in certain dissections at deep planes.

There is yet a third way of holding this bistoury, that is to hold it as if it were a pencil holder, letting the handle rest outside the hollow of the hand on the interdigital space between the thumb and the index finger. In this position the stabilizer is supported against the interdigital space.

It is possible for those skilled in the art to device variations of detail without departing from the spirit of the invention, wherefore those variations must be considered as falling within the scope of protection of this invention.

What is claimed is:

1. A bistoury handle comprising first and second elongate members each having first and second ends, the first elongate member being provided at its first end with means for gripping a blade and having a straight portion extending from its end and a curved portion extending from said straight portion towards its second end, said second elongate member being straight and being joined at its first end to the first elongate member at a point adjacent said first end thereof and being joined at its second end to the first elongate member at said second end thereof, holding means for engaging at least one of the surgeon's fingers thereby to hold said second member against movement, said holding means comprising a plate-like member secured to the second elongate member intermediate the ends thereof, the angle, measured in the common plane of the second elongate member and the straight portion of the first elongate member, between the plane of the plate-like member and the longitudinal axis of the second elongate member lying between the plate-like member and the first end of the second elongate member being substantially in the range from 112° to 115°, and the angle, measured in the plane perpendicular to said common plane and intersecting said longitudinal axis, between the plane of the plate-like member and said longitudinal axis lying between the plate-like member and said second end of the second elongate member being substantially in the range from 65° to 75°, the curvature of the curved portion of the first elongate member being adapted to fit in the hollow of the hand while the middle and ring fingers extend about the second elongate member, one on each side of said plate-like member.

2. A bistoury handle as claimed in claim 1, wherein the joint between said first end of said first elongate member and said fitting end of said second elongate member defines a groove extending longitudinally of the handle, the groove being positioned to support the thumb when the curved portion of the first elongate member is received in the palm of the hand and the middle and ring fingers extend around the second elongate member, one on each side of the plate-like member.

* * * * *

UNITED STATES PATENT AND TRADEMARK OFFICE
CERTIFICATE OF CORRECTION

PATENT NO. : 4,140,123
DATED : February 20, 1979
INVENTOR(S) : Pedro D. Curutchet It is certified that error appears in the above-identified patent and that said Letters Patent are hereby corrected as shown below:

On the cover sheet, left column, in ICIREPAT [54] "LANCETS"

should read-- BISTOURY HANDLES--; and between ICIREPAT [22] and

ICIREPAT [51] should be inserted

-- [30] Foreign Application Priority Data

Jul. 14, 1976 [AR] Argentina.................263954--

On page 1, top of column 1, "LANCETS" should read

-- BISTOURY HANDLES--.

Signed and Sealed this

Third Day of July 1979

[SEAL]

Attest:

Attesting Officer

LUTRELLE F. PARKER
*Acting Commissioner of Patents and Trademarks*